United States Patent [19]

Bhargava et al.

[11] Patent Number: 4,883,650

[45] Date of Patent: Nov. 28, 1989

[54] RADIOIDOHIPPURIC ACID ESTER, A CONJUGATE THEREOF, AND METHODS OF MAKING THE SAME

[75] Inventors: Kuldeep K. Bhargava, Bronx; Lakshman R. Chervu, Larchmont; M. Donald Blaufox, Rye, all of N.Y.

[73] Assignee: ALbert Einstein College of Medicine - of Yeshiva University, Bronx, N.Y.

[21] Appl. No.: 181,229

[22] Filed: Apr. 13, 1988

[51] Int. Cl.$^4$ .................. A61K 49/02; A61K 39/395; C07D 207/46

[52] U.S. Cl. ..................................... 424/1.1; 548/542; 530/389; 530/402

[58] Field of Search ................. 424/1.1; 530/402, 389, 530/324, 350; 548/542

[56] References Cited

U.S. PATENT DOCUMENTS 3,859,429  1/1975  Elias ..................................... 424/1.1
4,057,618  11/1977  Salmon et al. ....................... 424/1.1

FOREIGN PATENT DOCUMENTS 2195361  8/1987  Japan ................................. 548/542

OTHER PUBLICATIONS

Rohrbach, M.S. "[Glycine-1-$^{14}$C]Hippuryl-L-Histidyl-L-Leucine]" analytical Biochemistry, 84,272-276 (1978).

*Primary Examiner*—John S Maples
*Attorney, Agent, or Firm*—Amster, Rothstein & Ebenstein

[57] ABSTRACT

The novel N-hydroxysuccinimide ester of iodohippuric acid (IH-OSU), capable of forming a stable conjugate with a protein. The iodohippuric acid is preferably orthoiodohippuric acid (OIH) and radiolabeled. A protein compound useful as a radiolable comprises a stable conjugate of a protein and the N-hydroxysuccinimide ester of radiolabeled iodohippuric acid.

7 Claims, No Drawings

RADIOIDOHIPPURIC ACID ESTER, A CONJUGATE THEREOF, AND METHODS OF MAKING THE SAME

BACKGROUND OF THE INVENTION

The present invention relates to an ester of iodohippuric acid, and more particularly to a radiolabeled ester of iodohippuric acid, a stable conjugate thereof with a protein and a method of making the same.

Radioiodine labeled proteins of high specific radioactivities have wide application in a variety of biochemical studies. Specific antibodies labeled with various radionuclides are increasingly being applied for visualizing undetectable tumors and metastases. In addition, labeled antibodies offer a means of radioimmunotherapeutic ablation of tumors for which conventional therapies are ineffective.

A variety of procedures for labeling large molecules (e.g., macromolecules such as proteins) with radioiodine have been developed over the years. The most widely used chloramine-T procedure offers an efficient method for the substitution of iodine into the tyrosine residues of protein molecules and antibodies. However, some disadvantages of this procedure are: (i) polypeptides that lack tyrosine cannot be iodinated; (ii) oxidizing and reducing agents denature the protein to a certain extent. The rapid metabolism of radioiodinated antibodies leads to the incorporation of metabolized radioiodine into the thyroid and high levels of circulating radioiodine in the blood mask tumor uptake considerably.

The radioiodine-labeled iodohippuric acid, and in particular the ($^{125}$I)-orthoiodohippuric acid (OIH), would be a suitable radiolabel if it could be conjugated with proteins and antibodies under reaction conditions which would not adversely affect the components of the protein. The ($^{125}$I)-OIH-labeled protein offers the advantage of rapid blood clearance of the radioiodine labeled hippuran moiety upon metabolic breakdown of the conjugate so that the target-to-background ratio would be enhanced at short time intervals after injection with the conjugate and the risk to patient health from radioactivity minimized.

Accordingly, it is an object of the present invention to provide a novel ester of iodohippuric acid when can be radiolabeled.

Another object is to provide a radiolabeled ester of iodohippuric acid which is capable of forming a stable conjugate with a macromolecule such as a protein, especially under mild conditions.

A further object is to provide a protein compound useful as a radiolabel comprising a stable conjugate of a radiolabeled ester of iodohippuric acid and a protein, which conjugate upon metabolic breakdown provides rapid clearance of the radiolabeled hippuran moiety.

SUMMARY OF THE INVENTION

The above and related objects are obtained in one or more aspects of the present invention. The first aspect of the present invention is the N-hydroxysuccinimide ester of iodohippuric acid, hereinafter "IH-OSU." Preferably, the iodohippuric acid (IH) is orthoiodohippuric acid (OIH) and is radiolabeled. Radiolabeled IH-OSU is capable of forming a stable conjugate with a protein.

Another aspect of the present invention is a protein compound useful as a radiolabel comprising a stable conjugate of a protein and the radiolabeled IH-OSU.

A further aspect of the present invention is a method of forming a radiolabel capable of forming a stable complex with a protein comprising coupling radiolabeled iodohippuric acid with Di-(N-succinimidyl) carbonate (DSC).

A final aspect of the present invention is a method of forming a radiolabeled protein using the steps of forming radiolabeled hippuric acid IH-OSU and forming a stable complex of a protein therewith.

The radioactive ester OIH-OSU enables the labeling of proteins, such as human serum albumin, in a simple efficient manner. Organ distribution in mice and rats for the labeled albumin preparation and the commercial radioiodinated serum albumin (RISA) is similar. Hippuran metabolite released into the blood stream from the labeled conjugate upon metabolic breakdown results in rapid urinary clearance of the radiolabel. The hippuran labeling method offers a mild and rapid protocol for radioiodine labeling of proteins (including antibodies) for application in diagnostic nuclear medicine procedures.

DETAILED DESCRIPTION OF THE PREFERRED EMBODIMENTS

One aspect of the present invention comprises the novel N-hydroxysuccinimide ester of iodohippuric acid (IH-OSU) capable of forming a stable conjugate with a protein. The iodohippuric acid is preferably orthoiodohippuric acid (OIH), although the meta and para isomers may also be used. The iodohippuric acid may be cold (non-radioactive) or carry a radioiodine label, e.g., $^{131}$I, $^{123}$I and $^{125}$I.

Preparation of OIH-OSU

In order to prepare the N-hydroxysuccinimide ester of iodohippuric acid, hereinafter OIH-OSU, molar equivalents of cold OIH and Di-(N-succinimidyl) carbonate (DSC) were mixed with pyridine (to render the pH slightly basic) in dimethylformamide solvent (DMF), with stirring at room temperature overnight. The pyridine and DMF solvent were then flash evaporated, and repeated crystallization (2-3 times) of the residue from ethylacetate petroleum ether gave the OIH-OSU ester as a pure product. The OIH-OSU active ester was isolated in pure form with a melting point of 205°-207° C. Its structure was confirmed by carbon-hydrogen-nitrogen (CHN) analysis and nuclear magnetic resonance (NMR) spectroscopy as follows:

CHN Analysis: Calc'd for $C_{13}H_{11}N_2O_5I$: C, 38.83; H, 2.73; N, 6.96.

Found C, 38.96; H, 2.62; N, 7.01.

NMR (Me$_2$SO-d$_6$): 3.28 (S, 4H), 4.42 (dl, J=2.2 Hz 2H), 7.2-7.54(m, 3H), 7.94 (d, J=3.8 Hz 1H), 9.0(S, 1H).

The labeled ester OIH-OSU may be prepared from the cold ester, substituting radioactive iodine for cold iodine, but the following procedure for its preparation is preferred.

Preparation of ($^{125}$I)-OIH was carried out as per the known procedure of Elias. Elias, H. et al., *International Journal of Applied Radiation and Isotopes* (1973), Vol. 24, pp. 463-469. Silica gel thin layer chromatography using a solvent system (n-butanol:glacial acetic acid:water; 6:1.5:2.5) yielded purity greater than 96%.

Preparation of the labeled OIH-OSU ester was carried out using an equimolar mixture of labeled OIH (6 mg), DSC (5.1 mg), and pyridine (1.7 mg) in 150 ul of DMF and stirring for 2 hours at room temperature under dry conditions. It is believed that a reaction time of two hours suffices to complete the reaction.

Ester formation proceeds according to the following reaction:

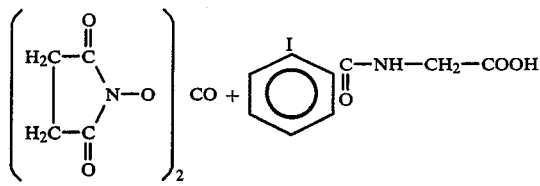

The reaction mixture containing ($^{125}$I)-OIH-OSU ester was used without any further separation to conjugate and hence label human serum albumin (HSA).

The ester of the present invention may also be formed by coupling radiolabeled OIH with N-hydroxysuccinimide carbonate in the presence of dicyclo hexyl carbodiimide, however, this requires a cumbersome preparation procedure and an eventual separation of insoluble urea from the reaction mixture.

Synthesis of ($^{125}$I)-OIH-Conjugated Albumin

To synthesize ($^{125}$I)-OIH-conjugated albumin by the coupling of the above ester with an excess of albumin, 50 μl of the above reaction mixture was added to 1 ml of human serum albumin solution (7 mg/ml) in 0.01M sodium phosphate buffer (pH 7.0), mixing every 10 minutes for a half hour. Coupling efficiency was determined to be 30 to 50% using dialysis procedure, and the efficiency did not improve with prolonged reaction time. There was no change in initial and final pH of the reaction mixture. The conjugate is believed to be formed by the production of an amide bond between the ester and the amino group of a lysine residue of the protein. The impurities in the reaction mixture—unreacted N-hydroxysuccinimide and OIH and free iodide—are non-reactive to protein and thus may be separated by dialysis or simple gel filtration.

Gel filtration of an aliquot of the labeled albumin prepared above on a 21.8×1.8 cm Sephadex G-100 column using 0.01M sodium phosphate buffer (pH 7) gave an elution profile indicating separate peaks for the protein, free hippuric acid and free iodide. The elution profile of commercial radioiodinated serum albumin (RISA) was in close agreement with that of the coupled protein prepared above. Incorporation of 38–50% of the radioactivity (mean 44.3%) was found in the conjugate in three preparations when the protein was purified through the column. RISA and unlabeled albumin gave retention times of 8.56 min and 8.69 min, respectively, by HPLC method.

Another aliquot of the conjugated protein was purified by dialysis at 5° C. against phosphate buffer (2 l.×2) using spectropor membrane tubing for 3 days. The three day dialyzed preparation showed the albumin activity at the same peak volume in gel filtration. High pressure liquid chromotography (HPLC) analysis of the dialysis bag contents gave a single radioactive peak volume at $T_r = 8.59$ min. HPLC was carried out in an isocratic mode on a DuPont 850 HPLC chromatography system using Zorbax GF 250 column with mobile phase as 0.1M sodium phosphate buffer at pH 7 and UV detection at 280 nm.

The ($^{125}$I)-OIH-conjugated HSA thus formed was analyzed by SDS polyacrylamide gel electrophoresis. Labeled albumin samples in phosphate buffer were applied to 10% acrylamide slab gel and protein fractions visualized with commassie blue strain.

Animal Studies:

Biodistribution studies of the labeled protein of the present invention at 60 min, 120 min and 240 min were carried out in CD-1 male adult mice (Charles River) with a dialyzed preparation (7 mg protein/ml) and in adult male rates (Sprague Dawley) with a gel separated preparation. Biodistribution studies of commercial radioiodine labeled albumin preparation (RISA) in animals of both species were carried out for comparison with the labeled protein of the present invention. The injectate consisted of 0.1 ml containing 1–3 uCi of ($^{125}$I) activity for all biodistribution studies.

The biodistribution data for the ($^{125}$I)-OIH conjugated albumin prepared above and for the commercial RISA are almost identical. Thus the biodistribution data indicate that the iodine labeled proteins of the present invention have biodistribution properties similar to iodine labeled proteins prepared by direct radioioidination (i.e., commercial RISA). The biodistribution data showing identical behavior in animals between the OIH labeled albumin of the present invention and commercial RISA suggest that the synthetic methods of the present invention did not effect any change in the albumin molecule. However, upon metabolic breakdown of these materials, a substantial difference will be appreciated. The RISA upon metabolic breakdown undergoes a deiodination which leaves the iodide largely in circulation for prolonged periods. This gives rise to a large body of background radioactivity, with the iodide accumulating in the thyroid gland. On the other hand, the OIH-labeled albumin of the present invention upon metabolic breakdown gives rise to a hippuran moiety which is rapidly eliminated from the body via the urinary tract. More particularly, at 4 hours post administration, urinary excretion of radioactivity from the labeled protein prepared above was over four times that from commercial RISA and there was no accumulation of activity in thyroid. In the case of OIH coupled albumin of the present invention, rat urine analysis by instant thin layer chromatography (ITLC) and high pressure liquid chromatography (HPLC) showed that the activity corresponded to ($^{125}$I)-OIH Accordingly, the ester of the present invention provides a viable method for radioiodide labeling of macromolecules such as antibodies and other proteins for application in diagnostic nuclear medicine procedures for imaging without the annoying background of free circulating iodide in the blood pool for prolonged periods and with a lesser health risk from radioactivity to the patient than other methods of iodination.

As the labeled ester is quite stable, it can be supplied in a kit form (the kit also containing the solvent) for ready labeling with any large molecule. While the present application uses human serum albumin as a model system to test the incorporation of the labeling moiety via the succinimide ester, clearly the same labeling moiety may be incorporated in other macromolecules via the same succinimide ester. The incorporation reaction proceeds rapidly with good yields under gentle conditions, apparently without any indication of degradation or aggregation of the protein molecule. The proposed procedure involves no harsh chemical environment during labeling and permits the incorporation of a large amount of radioactivity on the protein, even though a given protein may be modified in only a single site.

More particularly, the ester can be coupled to a protein in aqueous solution at room temperature. The labeled protein may be purified readily by gel separation or by dialysis.

To summarize, the present invention discloses the synthesis of the N-hydroxysuccinimide ester of IH, and in particular the ester of radioactive OIH, the ester being adapted for conjugation with human serum albumin and other proteins under mild conditions in aqueous solution at neutral pH. The ($^{125}$I)-OIH-labeled protein offers rapid blood clearance of the radioiodide labeled hippuran moiety upon metabolic breakdown relative to commercial radioiodinated serum albumin (RISA) and thus diminishes the health danger to the patient from radioactivity and enables an enhanced target-to-background ratio at short time intervals after injection.

Now that the preferred embodiments of the present invention have been described in detail, various modifications and improvements thereon will become readily apparent to those skilled in the art. Accordingly, the appended claims are to be construed broadly in a manner consistent with the spirit and scope of the present invention.

What we claim is:

1. The N-hydroxysuccinimide ester of iodohippuric acid wherein said iodohippuric acid is radioiodinated.

2. The ester of claim 1 wherein said iodohippuric acid is radioiodinated orthoiodohippuric acid.

3. A compound capable of forming a stable conjugate with a protein comprising the N-hydroxysuccinimide ester of radioiodinated iodohippuric acid.

4. The compound of claim 3 wherein said iodohippuric acid is orthoiodohippuric acid.

5. A protein compound useful as a radiolabel comprising a stable conjugate of a protein and the N-hydroxysuccinimide ester of radioiodinated iodohippuric acid.

6. The compound of claim 5 wherein said iodohippuric acid is orthoiodohippuric acid.

7. The compound of claim 5 wherein said protein is an antibody.

* * * * *